(12) United States Patent
Garth

(10) Patent No.: US 6,964,644 B1
(45) Date of Patent: Nov. 15, 2005

(54) BACK BRACE

(76) Inventor: Geoffrey C. Garth, 34 57th Pl., Long Beach, CA (US) 90803

( * ) Notice: Subject to any disclaimer, the term of this patent is extended or adjusted under 35 U.S.C. 154(b) by 53 days.

(21) Appl. No.: 10/412,908

(22) Filed: Apr. 14, 2003

Related U.S. Application Data

(63) Continuation-in-part of application No. 09/323,291, filed on Jun. 1, 1999, now abandoned, and a continuation of application No. 09/785,597, filed on Feb. 16, 2001, now abandoned.

(51) Int. Cl.$^7$ .............................................. A61F 5/00
(52) U.S. Cl. ...................................... 602/19; 128/876
(58) Field of Search ............................. 602/19, 18, 23, 602/5; 128/96.1, 99.1, 102.1, 876, 869, 846, 128/100.1, DIG. 15; 2/2, 337, 338, DIG. 3

(56) References Cited

U.S. PATENT DOCUMENTS

| | | | | |
|---|---|---|---|---|
| 2,554,337 A | * | 5/1951 | Lampert ..................... | 606/237 |
| 4,843,688 A | * | 7/1989 | Ikeda .......................... | 24/170 |
| 5,111,807 A | * | 5/1992 | Spahn et al. ................ | 606/244 |
| 5,230,698 A | * | 7/1993 | Garth .......................... | 602/18 |
| 5,363,863 A | * | 11/1994 | Lelli et al. .................. | 128/876 |
| 5,450,858 A | * | 9/1995 | Zablotsky et al. .......... | 128/876 |
| 5,500,959 A | * | 3/1996 | Yewer, Jr. .................... | 602/19 |
| 5,622,529 A | * | 4/1997 | Calabrese .................... | 602/18 |
| 5,690,609 A | * | 11/1997 | Heinze, III .................. | 602/19 |
| 5,830,167 A | * | 11/1998 | Jung ............................ | 602/19 |
| 5,853,378 A | * | 12/1998 | Modglin ...................... | 602/19 |
| 5,911,697 A | * | 6/1999 | Biedermann et al. ........ | 602/19 |

* cited by examiner

Primary Examiner—Michael A. Brown
Assistant Examiner—Huong Q. Pham
(74) Attorney, Agent, or Firm—Rutan & Tucker

(57) ABSTRACT

A back brace has left, right and back panels that substantially overlap to form a tubular back brace when worn. Leverage multiples tightening force during tightening. After each successive tightening by the lever, retaining bands retain the back brace in position. Pressure spreading layers have a secondary adjustment mechanism comprising a plurality of notches extending inward from upper and lower edges, and at least one hole aligned with each of the plurality of notches. The back panel has a window overlying the sacrum. The orthopedist can observe the engagement of the back brace in this area through the window. A malleable bar is attached to the back panel adjacent the window so that the orthopedist can adjust the malleable bar for proper fit. After the initial fitting, including adjustment of the back panel over the sacrum, the back brace may be readily donned and doffed by the patient.

15 Claims, 11 Drawing Sheets

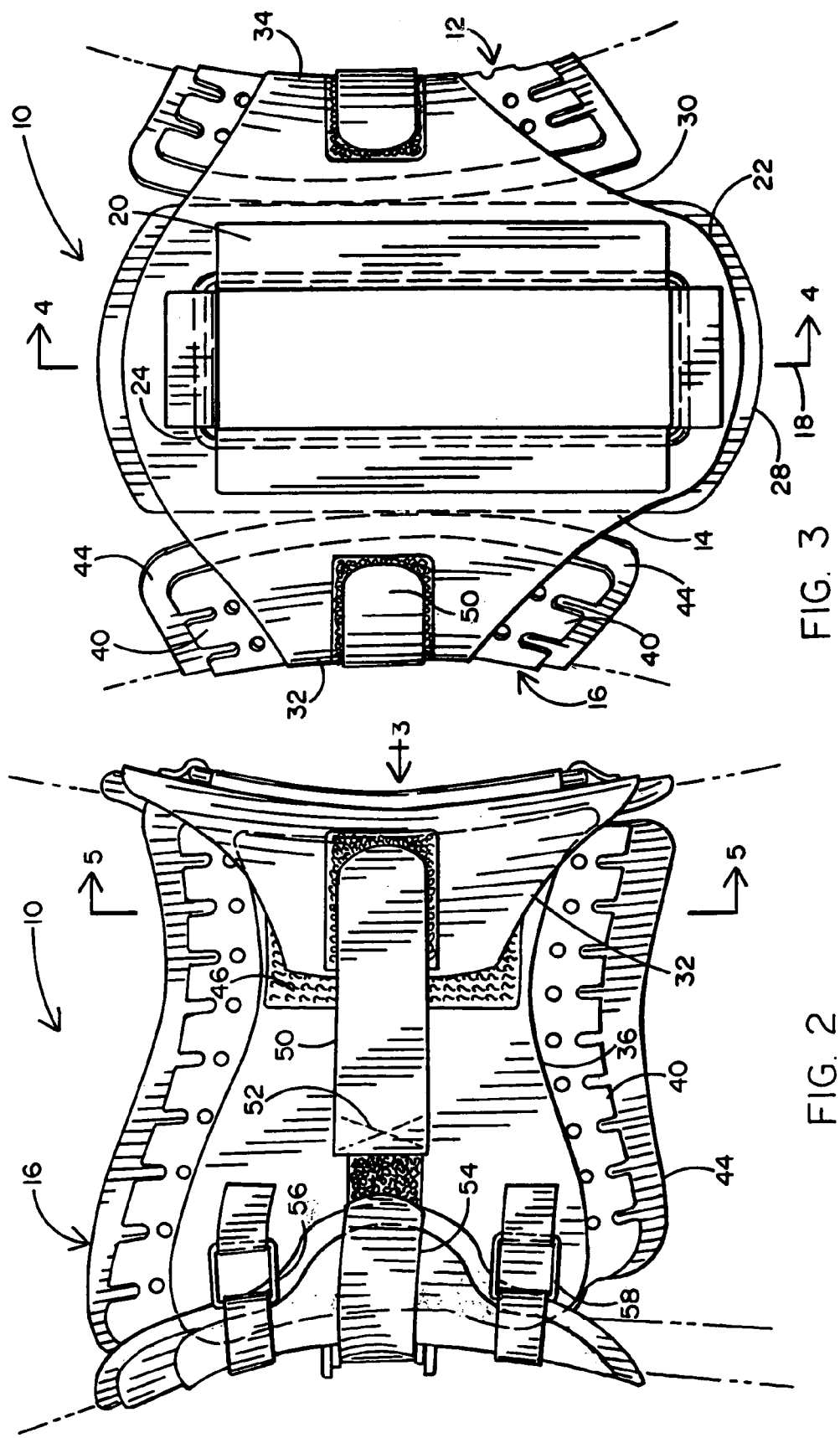

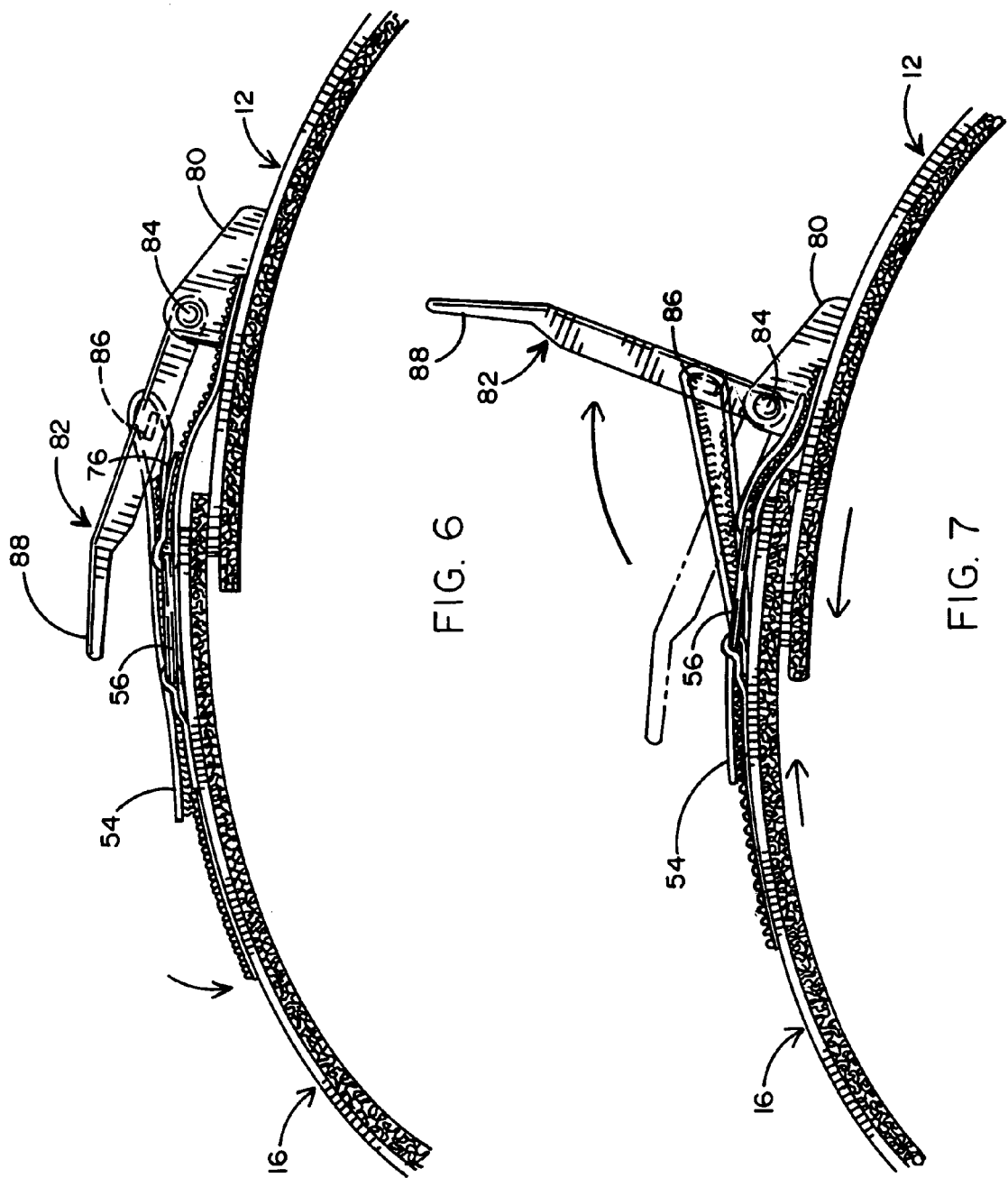

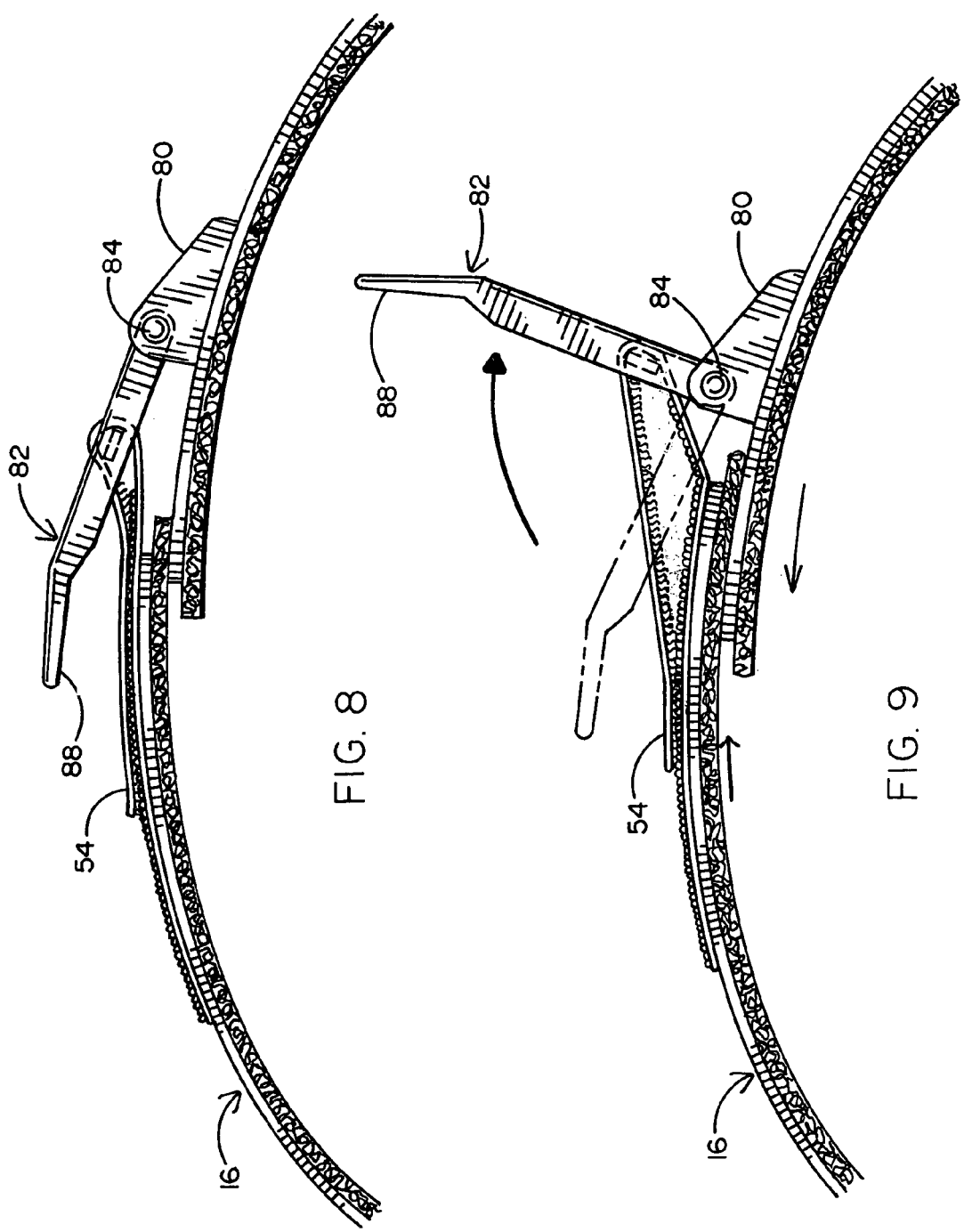

US 6,964,644 B1

BACK BRACE

CROSS-REFERENCE

This application is a continuation-in-part of my previous application Ser. No. 09/323,291, filed Jun. 1, 1999 (now abandoned), and is a continuation of my previously filed application Ser. No. 09/785,597 filed Feb. 16, 2001, now abandoned for "Back Brace", the entire disclosures of which are incorporated herein by this reference.

FIELD OF THE INVENTION

This invention is directed to a back brace which surrounds the mid-torso of the patient with three overlapping panels secured to each other to form a tubular back brace. The tubular back brace has a window in the back panel with an adjacent malleable frame which can be bent to conform to the patient. A single lever step-by-step tightening structure permits the patient to achieve easily adequate circumferential tension when he redons the back brace after an initial fitting.

BACKGROUND OF THE INVENTION

A number of muscular and orthopedic problems are present in the human patient above the sacrum. There are a number of different corset-like structures and partial body belts which presumably engage around and hold the mid-section of a patient having a back problem. These are intended to be back supports which overcome deficiencies in the musculature and orthopedic structure. When such back supports are properly fitted, they can do a very good job, but are expensive due to the individualized fitting thereof, which sometimes includes individual part shaping. On the other hand, if they are not fitted to the sacro portion and the vertebrae directly thereabove, such back braces are not fully effective. Additionally, the edges of such back braces take all of the load when motion is attempted, which can bruise the tissue directly under the edge, which can lead to the patient loosening the brace, thereby reducing its effectiveness.

SUMMARY OF THE INVENTION

In order to aid in the understanding of this invention, it can be stated in essentially summary form that it is directed to a back brace formed of three panels which overlap to completely embrace the patient's midsection. The three panels are a back panel and left and right side panels. The left and right side panels each overlap the back panel and are adjustably secured thereto. When embracing the patient, the left and right side panels also overlap to form a tubular back brace which completely embraces the patient's mid-section. The back brace may have a malleable section in the back panel above the sacrum and a window adjacent thereto so that the fitter can observe and adjust the most critical portion of the fitting operation: against the back, above the sacrum. Both the left and right panels overlap the back panel in an adjustable way to permit adjustment of the total circumferential length to fit persons of different size. Tightening is preferably by a multiple step lever action permits even a weak person to tighten the back brace on himself with proper tension.

It is a purpose and advantage of this invention to provide a back brace which is suitable for use on persons of different size by virtue of substantially overlapping panels of at least two which are suitable for size adjustment. When adjusted, the panels are firmly attached to each other. They are non-hinging and non-pivoting of the panels at the contacting surfaces of the panels.

It is another purpose and advantage of this invention to provide a back brace which is comprised of left and right side panels together with a back panel. The panels are overlapping with respect to each other, and the left and right side panel are each adjustable with respect to the back panel and are attached so that the left and right side panels are non-rotatable with respect to the back panel when the adjustment is secured so that the back brace is semi-permanently adjusted to the physiological back brace requirements of a particular patient.

It is another purpose and advantage of this invention to provide a back brace which has a step-by-step lever action system to multiply the force achieved in tightening the back brace, even by patients having limited strength.

It is another purpose and advantage of this invention to provide a back brace which has a malleable material adjacent the sacrum when the back brace is worn, so that the portion of the back brace at the sacrum and at the vertebrae thereabove may be malleably adjusted in compound curvature to optimize the fit in this region, together with a window adjacent the malleable structure so that fitting may be observed at the malleable portion even while the back brace is in tension on the person being fitted so that the back brace not put pressure on the bony structure of the spine.

It is a further purpose and advantage of this invention to provide a pressure spreading layer which has notches in the edge and holes in alignment with the notches so that customized adjustment of the flexure of the edge can be achieved by cutting to the hole to increase flexibility at the edge.

Other purposes and advantages of this invention will become apparent from a study of the following portion of the specification, the claims and the attached drawings.

BRIEF DESCRIPTION OF THE DRAWINGS

FIG. 2 is a left-side elevational view thereof when it is positioned on a patient.

FIG. 3 is a rear elevational view thereof, as seen generally from the arrow 3 of FIG. 2.

FIG. 6 is a downward-looking view of the tightening mechanism at the beginning of its tightening step.

FIG. 7 is similar view showing the tightening lever pulled about half way through the tightening stroke.

FIG. 8 is a downwardly looking view similar to FIG. 6, but with the nearby retaining band removed from the view to better illustrate the tightening motion.

FIG. 9 is similar to FIG. 7, with the near side retaining band removed from the view.

DESCRIPTION OF THE PREFERRED EMBODIMENTS

Figure 1:
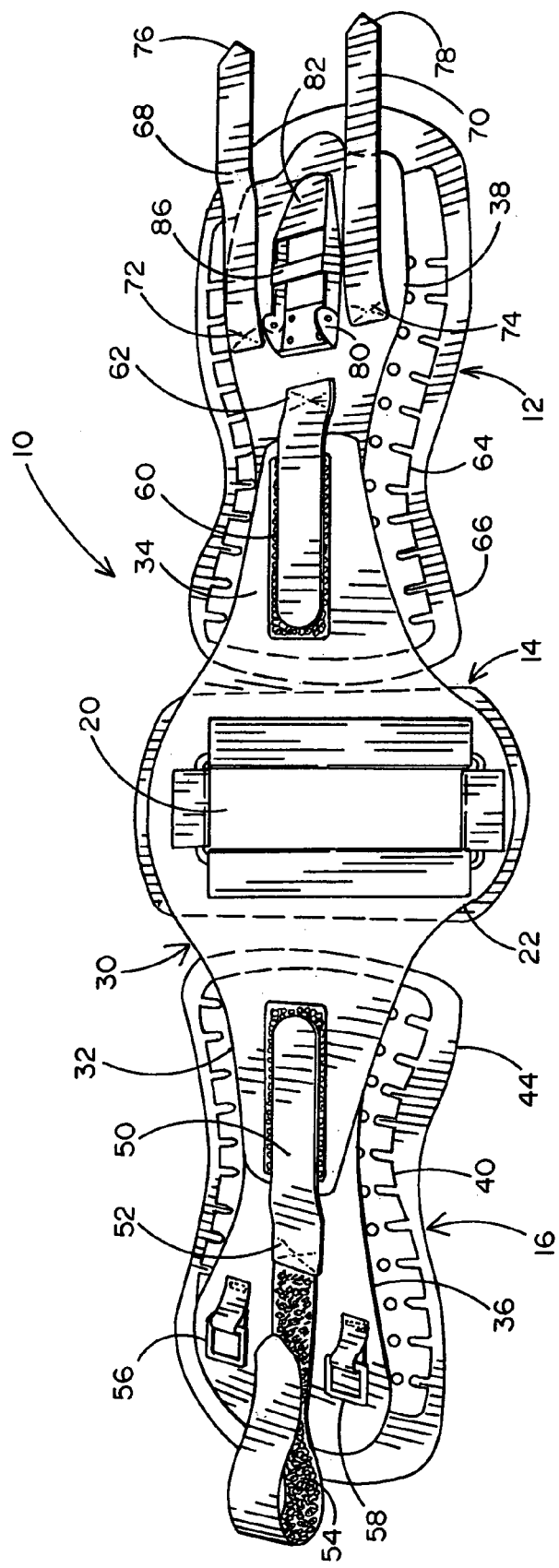
FIG. 1 is a substantially rear-elevational view of the first preferred embodiment of the back brace of this invention in the open position.
Figure 4:
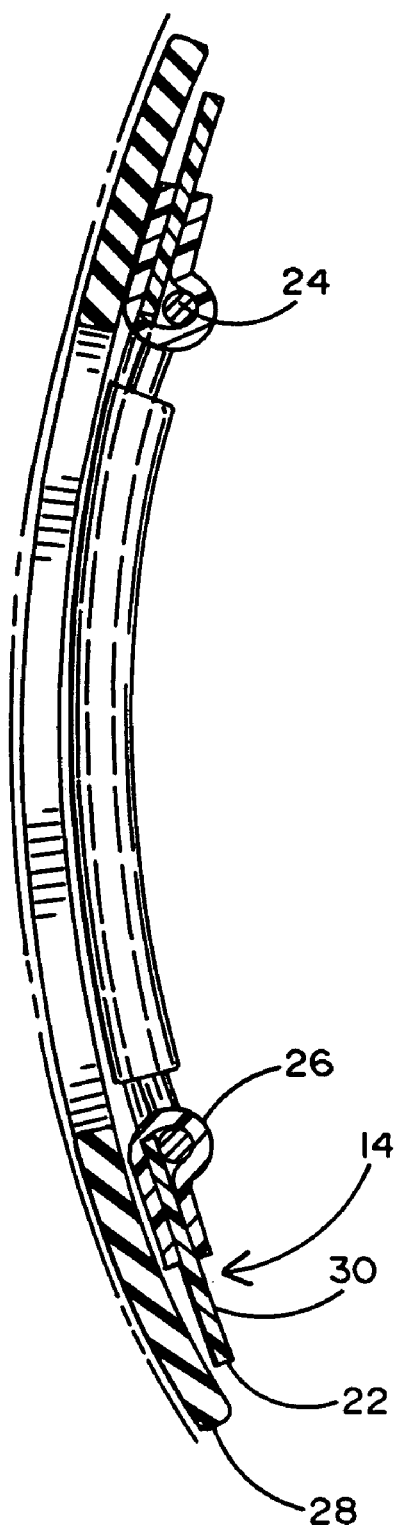
FIG. 4 is an enlarged section through the back of the back brace, as seen generally along line 4—4 of FIG. 3.

The first preferred embodiment of the back brace of this invention is generally indicated by the numeral 10 and is shown in a spread-out view in FIG. 1, is shown in left side elevation in FIG. 2, is shown in rear elevation in FIG. 3, and is shown in front elevation in FIG. 9. The back brace 10 comprises three panels which overlap with respect to each other when worn. These three panels comprise the right panel 12, back panel 14 and left panel 16. The back panel 14 has a center line 18, which is the section line upon which FIG. 4 is taken (see FIG. 3). When worn, the center line should overlie the patient's spine. The main body of the back panel is formed of flexible sheet synthetic polymer composition material which bends, but is not appreciably stretchy.

Window 20 is formed along the center line. The window extends upward from close to the bottom edge 22, which overlies the sacrum when worn. Attached to the back panel 14 around the window 20 is malleable bar 24. The malleable bar is preferably a solid aluminum rod for light weight and malleability. The malleable bar is shown as being a substantially rectangular structure to lie around window 20. It may extend only along the two sides or may be U-shaped. Protector 26, see FIG. 4, wraps around the malleable bar 24 to protect the bar and to attach it to the back panel 14. The protector has overlapping edges outside of the malleable bar which are attached to the back panel 14 by sewing, rivets or adhesive. The malleable bar and its attachment 26 are arranged so that they lie around the edge of the window. This structure is positioned so that the orthopedist can bend the malleable bar to shape the back panel of the back brace to the sacrum and spinal curvature of the patient. The window also gives additional freedom to the back panel so the back panel can be bent into compound curves near the window. The window is sufficiently large so that the orthopedist can insert his fingers into the window and run them up and down along the sides of the window to tactilely determine the fit of the back panel against the back of a patient. The window also permits viewing of the manner of engagement of the back panel against the patient to insure that the proper contact is provided.

The window is sufficiently tall along the length of the spine so that at least three vertebrae are exposed for visual and tactile observation of the fit of the back panel at that critical area of the back. The proper curvature and distribution of pressure of the back panel against the patient is important to both the comfort of the back brace and to provide of the proper orthopedic support to achieve the orthopedic goal. The orthopedist can visually and tactilely observe the engagement at the sacrum and against the lower back to derive optimum results.

Figure 5:
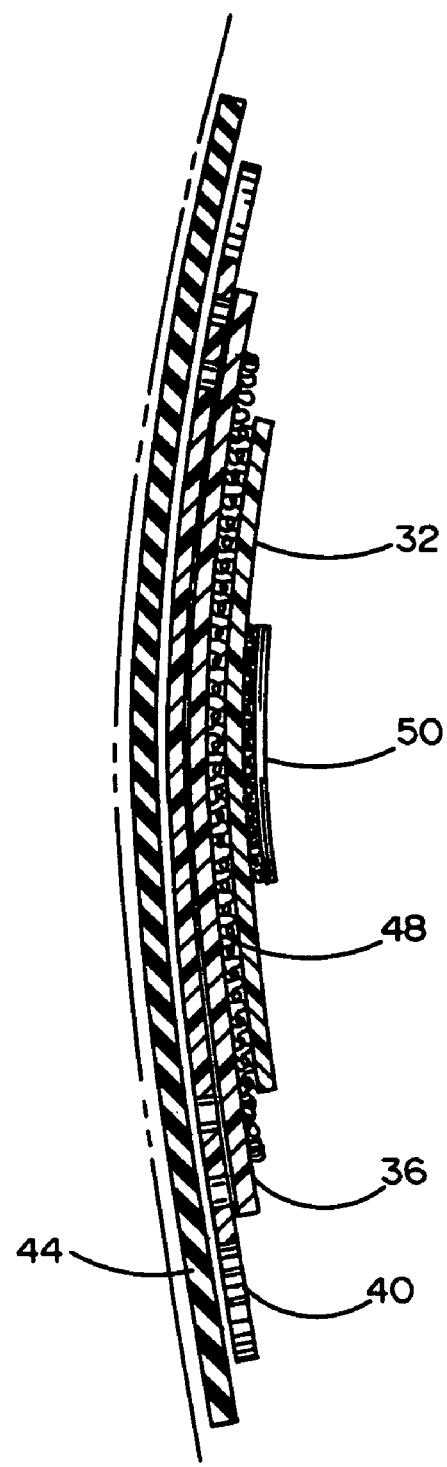
FIG. 5 is an enlarged section taken generally along line 5—5 of FIG. 2, showing the layers in the overlapping portion of the left side panel and the back panel which permit circumferential adjustment of the back brace.

Positioned on the interior of back panel 14 is a foam back panel cushion layer 28 which is attached to the interior of back panel 14 around the window. As is best seen in FIGS. 1 and 3, left and right wings 32 and 34 are formed as part of the back panel and extend to the left and right, respectively, for overlapping with the left panel 16 and right panel 12. The back body layer 30, which makes up the principal structural portion of the back panel is a layer of sheet synthetic polymer composition material. The same material forms a left body layer 36 and a right body layer 38. As seen in FIG. 1, the left and right wings of the back body layer overlie the left and right body layers. As seen in FIG. 5, on the inside of left body layer 36 is secured left pressure spreading layer 40 and foam cushion layer 44. The left wing of the back panel overlaps the left panel layer and is adjustably secured thereto by means of hook-and-loop fasteners. The portion of the hook-and-loop fastener on the left body layer 36 is seen at 46 in FIG. 2, and that which underlies the left wing 32 is seen at 48 in FIG. 5.

There is a circumferential direction at a right angle to the center line 18, and it is seen that the length of the circumference can be adjusted by selecting the placement of left wing 32 onto the hook-and-loop fastener on left body layer 36. As additional securement, band 50 is secured at attachment point 52 and overlies left wing 32. The underside of the band 50 and the upper side of wing 32 have cooperating hook-and-loop fasteners. After the left wing 32 is secured in place on left body layer 36, then the band 50 is attached to provide greater strength.

When the attachment is completed between the back panel and left panel and between the back panel and right panel, the back brace 10 is rigid in the sense that, except for bending around the patient, there is no motion between the left panel, back panel and right panel. When the back brace 10 is laid out in a plane, as seen in FIG. 1, there is no rotation of one panel with respect to another on an axis perpendicular to the plane of the paper. In a sense, the back brace 10 is a one-piece back brace because it acts like a one-piece back brace when the left and right panels are attached to the back panel and are attached to each other at the front. However, as noted above, the left panel and right panel are each preliminarily adjustable so that the total circumference of the back brace can be adjusted to the patient. Furthermore, when properly adjusted and when engaged around the patient, the left and right panels overlap over the belly of the patient to form a tubular back brace.

Mounted on the face of the left body layer 36 is tightening strap 54 which is also attached at securing point 52. Furthermore, attachment loops 56 and 58 are secured to the front of panel layer 36 above and below the tightening strap 54. The attachment loops 56 and 58 are positioned as high and as low (respectively) on panel 36 as possible. Enclosed around the patient, as seen in FIGS. 2, 3, 12 and 13, the left and right side panels overlap, and the two spaced straps 76 and 78 prevent rotation of the front of the left and right side panels around an axis generally perpendicular to the drawing in FIG. 13.

The right side panel 12 is similar to the left side panel 16 in an opposite-handed way. The right side panel body layer 36 is the principal strength member of the right side panel 12. The left side panel body layer 36 is of flexible sheet synthetic polymer composition material. Right wing 34 of the back panel 14 overlies left body layer 36. It is detachably and adjustably attached by means of a hook-and-loop fastener system, as previously described. In addition, band 60 is attached to left body layer 36 at attachment point 62. The band 60 is detachably attached to the exterior of right wing 34 by means of hook-and-loop fastener. This permits the right panel 12 to be adjusted along the circumferential line previously described.

The interior of right panel layer carries right pressure spreading layer 64 and right cushion foam layer 66. The right pressure spreading layer 64 is made of sheet synthetic polymer composition material of greater flexibility than the right panel 36. It may achieve this flexibility by being of lesser thickness.

The right side panel 12 also carries retaining bands 68 and 70 which are secured at their securing ends 72 and 74 to the right panel layer 38 as high and as low (respectively) as possible. The bands 68 and 70 extend through the loops 56 and 58 and have free ends 76 and 78 extending therefrom. These free ends have one-half of hook/loop fastener while the other half is on the outward face of the retaining bands 68 and 70 to hold the bands in place when they are carrying tension, see FIGS. 12 and 13. Since there are two widely spaced retaining bands 68 and 70 and since the three panels are secured to each other so that they act as one piece, the two side panels where they overlap at the front and are secured by the retaining bands 68 and 70 do not have any up and down freedom or rotative freedom with respect to each other. The upper and lower retaining bands 68 and 70 can be separately tightened to adjust the back brace for different physiological development. This adjustment permits proper fit of the back brace on persons having high or low hips/waist circumference ratio. Once the back brace is fitted and adjusted to a patient, it acts like a single piece back brace uniquely fitted for that particular patient. The three panels overlap on the sides and front and are secured so that there is no relative up and down or rotative motion between them.

The back brace 10 must be properly tightened. After the first adjustment by the orthopedist, the patient must be able to easily engage the back brace about himself each time he needs to use it. This may require more force than the patient can apply without mechanical advantage. A lever system which is repetitively used to tighten the back brace step-by-step is provided. Pivot bracket 80, see FIGS. 1 and 6-13, is secured to the front of right panel 12 between retaining bands 68 and 70. Tightening lever 82 is mounted on pivot pin 84. The tightening lever has cross bar 86 and a grasping surface 88 on the lever outward from the cross bar.

Figure 13:
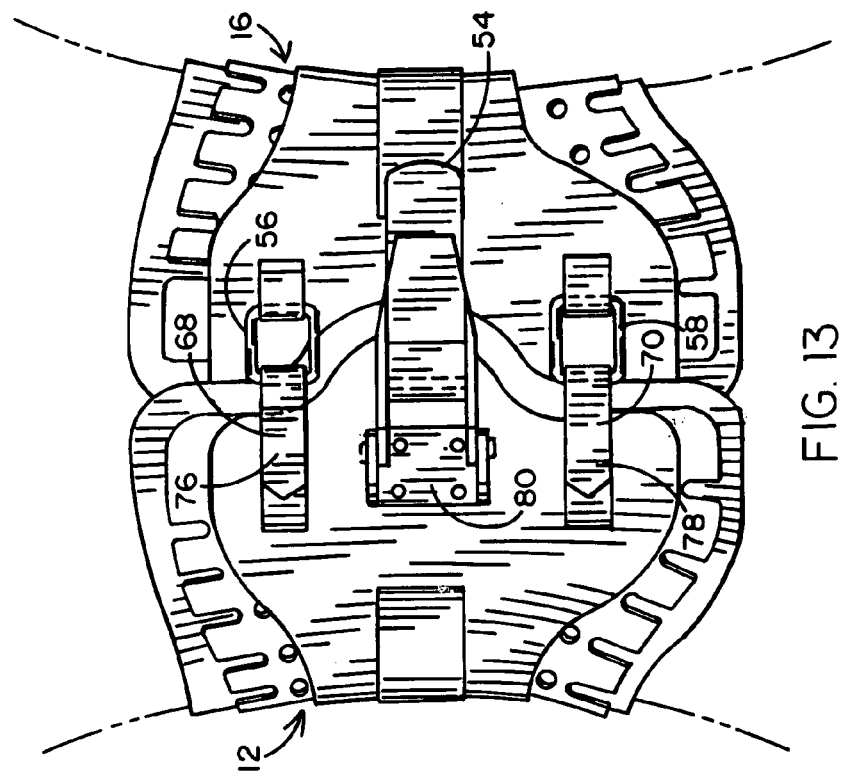
FIG. 13 is a front elevational view of the back brace as fully tightened on a patient.
Figure 12:
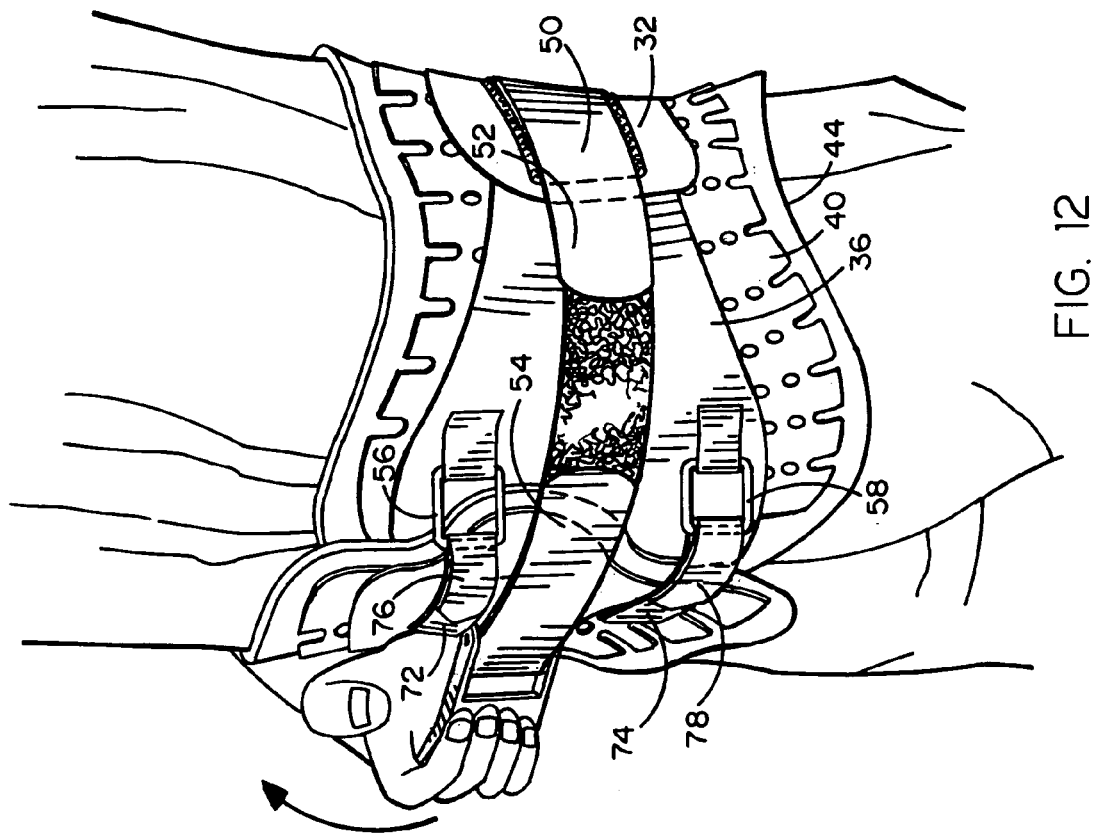
FIG. 12 is a perspective view of the back brace with tightening lever being moved in the tightening direction, similar to the position of FIGS. 6 and 9.

When the back brace 10 is first worn, the orthopedic specialist fits it to the patient. First, he opens the bands 50 and 60 and laterally shifts the left and right wings 32 and 34 of the back panel, respectively, on the left and right panels 16 and 12. This adjustment is for the waist circumference of the patient. The adjustment is made large enough so that the back brace can be engaged around the waist of the patient and loosely attached to hold the back brace generally in place before tightening. The open back brace is pulled around the torso and is arranged with the lower edge 22 on the sacrum. The ends of the left and right panels are pulled into an overlapping position shown in FIG. 12. In this position, the bands 68 and 70 are engaged through the loops and 58, as seen in FIG. 12. The ends 76 and 78 are pulled and laid down in hook-and-loop attachment as shown in FIGS. 12 and 13.

Figure 10:
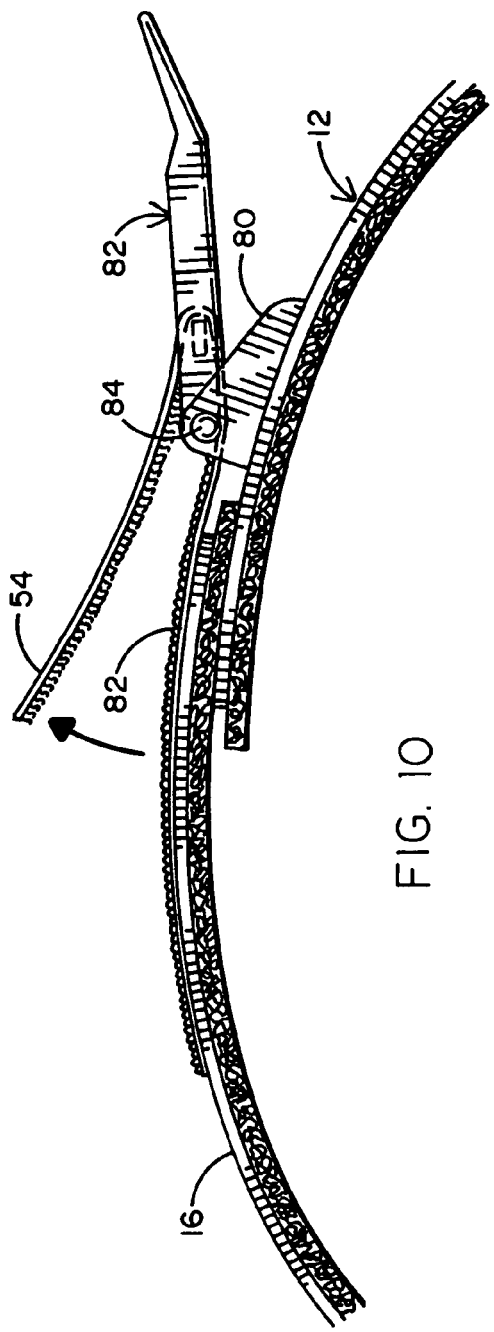
FIG. 10 illustrates the tightening lever in its fully deflected position when the retaining bands are tightened and the tightening strap is loosened for resetting.
Figure 11:
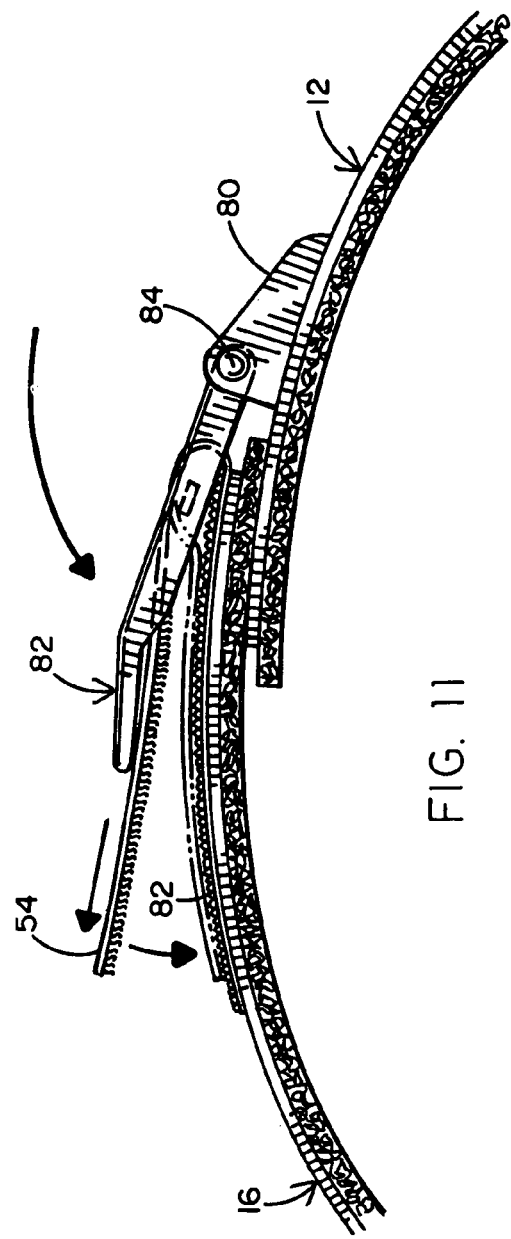
FIG. 11 is a similar view showing the tightening lever returned to its starting position and the tightening strap being reattached.

Tightening strap 54 is engaged around the cross bar 86 with the tightening lever in the left position shown in FIGS. 6 and 8. The end of the tightening strap 54 is laid down in the hook-and-loop fastener 82 to secure it. FIGS. 6 and 8 show this laying down and securement of the tightening strap 54. FIGS. 6 and 8 show the same position, but in FIG. 8, the view is below the retaining band 68 so that the view of the action of the lever 82 is not obscured. Similarly, FIG. 9 is in the same position as FIG. 7, but the view is from below retaining band 68 for the purpose of clarity. FIGS. 10 and 11, which depict later steps in the sequence, show the structure as seen from below the upper retaining band 68. Once the tightening strap 54 is secured in place, the lever 82 is grasped and pulled to the right from the position of FIG. 8 through the position of FIG. 9 to the position of FIG. 10. Due to the fact that the grasping surface 88 is farther from the pivot point 84 than the bar 86, the tightening force on tightening strap 54 is multiplied, as compared to the manual force applied by the patient to the handgrip 88 on the end of the tightening lever 82 away from pivot 84. As seen in FIG. 8, the force multiplication is about four times. The tightening lever is pulled by the patient to the right as he views it from above, as seen in FIGS. 6–11. When the lever is pulled to the far right, the retaining band 68 and 70 are retightened. The end of the tightening strap 54 is pulled loose, as is seen in FIG. 10, and the lever 82 is returned to the left position, as seen in FIG. 11. The tightening strap is again laid down in the hook-and-loop fastener 82 to secure it. The tightening lever 82 is pulled again and the retaining bands 68 and 70 are retightened. When the lever is pulled to the right to the position shown in FIG. 10, and before the tightening strap 54 is pulled loose, the retaining bands 68 and 70 are loose. Their ends 76 and 78 are disengaged, tightened and laid down again. Then the lever is returned to the left and the tightening strap is disengaged, retightened and attached. The pulling of the lever and tightening of the bands is repeated as required until the desired tightness is achieved. When the desired tightness is achieved, the end of strap 54 is laid down and retained by hook-and-loop fasteners. The free ends 76 and 78 are laid down to suit the patients development and retained by hook-and-loop fasteners as shown in FIG. 9.

During the initial fitting, the orthopedist inspects the fit of the back of the back brace against the sacrum and lower back vertebra through the window 20. He bends the bar adjacent the window so that proper back contact is achieved in this area. The presence of the window gives the orthopedist the opportunity to feel through the window 20 to determine the fit of the back brace in that area and to further position and configure as may be necessary for the proper fit of the back brace. It also permits the back panel to be formed into compound curves to appropriately contact the compound curves of the lower back. After the initial fit by the orthopedist, the back brace can be donned by most patients without assistance and tightened to the desired circumferential tension. The back brace completely overlaps at front and sides so as to provide a tubular back brace support structure. By loosening and tightening straps 54, 68 and 70, the patient may individually adjust the tightness of the back brace in accordance with his own comfort level.

The principal layers of each of the left, right and back panels are quite stiff. The foam cushion layer in each panel gives some cushioning effect. However, at the edges of the stiff panels, the transition between the stiff panel and foam cushion layer may be too great and present to the patient what feels like a sharp edge. It is for this reason that the pressure spreading layers 40 and 64 are fitted on the left and right panels. These layers are of polymer material of greater flexibility than the principal layer. Outward force occasioned by the body of the patient causes bending of these pressure-spreading layers to "round off" the edge. In order to permit soft bending at the transitional layers, notches are provided in the edge. In alignment with each of the notches is at least one hole with preferably two such holes presented, as seen in FIG. 12. If a particular area applies too much pressure on the patient's body, this can be softened by shearing the pressure-spreading layer from the notch to one or both of those aligned holes. Such cutting reduces the strength of the pressure-spreading layer at that point, allowing it to be bent into a compound curve to provide even more distribution of pressure. After appropriate fitting and modifications deemed necessary and appropriate, the orthopedist approves the fit and releases it to the patient.

Figure 14:
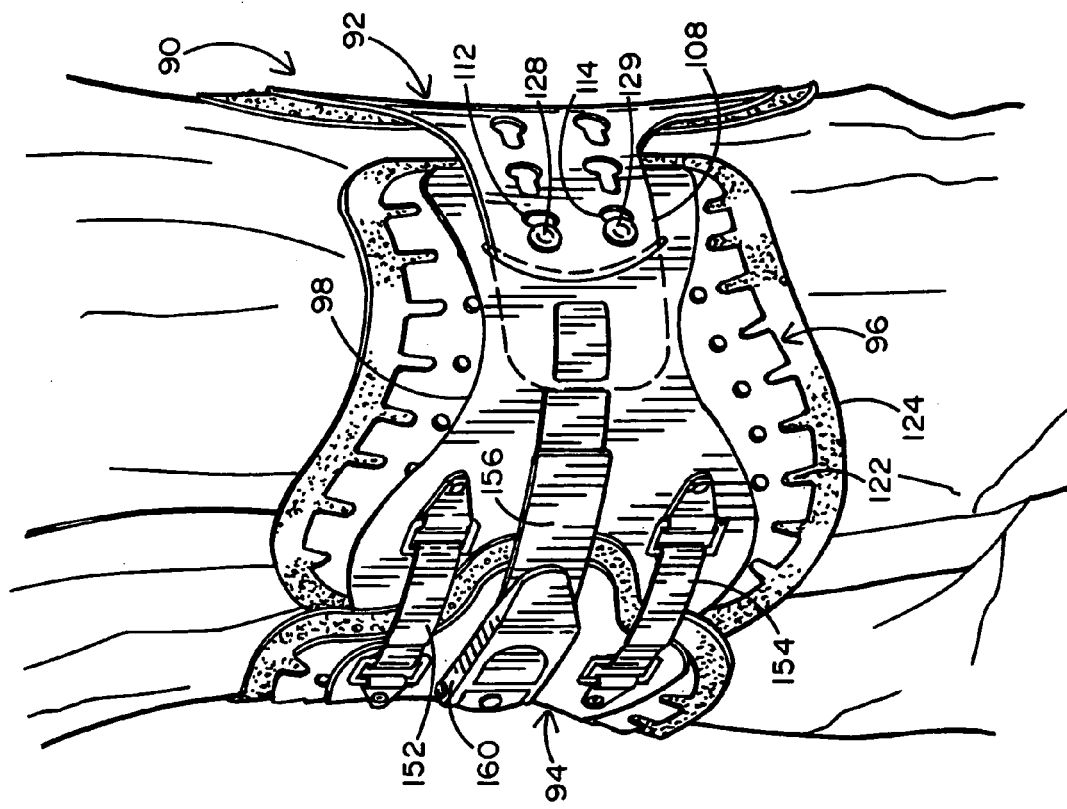
FIG. 14 is a perspective view of the second preferred embodiment of the back brace of this invention.

The second preferred embodiment of the back brace of this invention is generally indicated at 90 in FIG. 14. It is comprised of a back panel 92 (shown in FIG. 17), a right panel 94 (shown in FIG. 15), and a left panel 96 (shown in FIG. 16). The right and left nomenclature refers to the orientation when worn, as seen in FIG. 14. In that figure, the back brace 90 is shown as being worn by a patient in its tubular, closed form. The three panels are very similar to those represented in the back brace 10, but the attachment between the back panel and the left and right side panels, respectively, is different.

Back panel 92 is formed of a principal layer 98 of sheet synthetic polymer composition material which-is sufficiently thin and flexible to be able to bend around the torso, but is stiff enough to substantially retain its form. Secured to its front is a synthetic polymer foam layer 100. A window 102 is formed on the vertical center line of the back panel. The window has a malleable bar 104 at least on its left and right sides. The bar is held in place by a protector 106 the same is protector 26. The window is sufficiently tall to permit the orthopedist to examine the fit of the back panel against the patient's back. The observation can be made by inserting fingers into the area to determine if there is pressure or space. The window also permits visual examination of the fit. The malleable bar permits adjustment of this portion of the back panel to achieve the individualized fit required for maximum support and optimum comfort.

Figure 17:
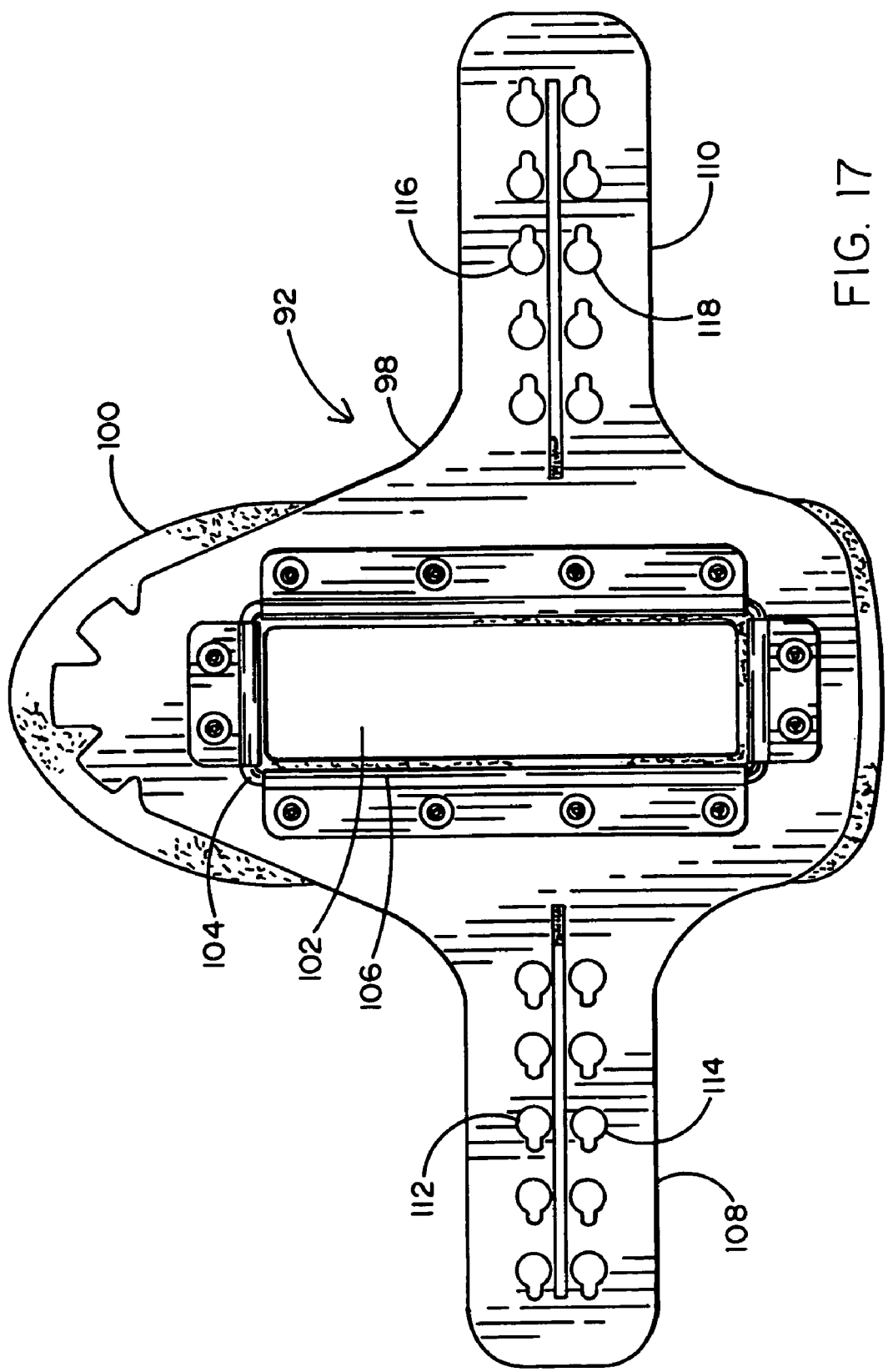
FIG. 17 is a plan view of the back panel used in overlapping association with the side panels of FIGS. 15 and 16.

The principal layer of the back panel has left and right tongues 108 and 110. The tongues are of uniform width and are substantially straight. The tongues have pairs of keyhole openings therein. The center pair of keyhole openings in the left tongue are shown at 112 and 114, and the center pair of keyhole openings in the right tongue are shown at 116 and 118. The keyhole openings are each formed of a larger circular opening with a smaller slot extending therefrom, extending in the direction away from the central upright axis of the back panel. As seen in FIG. 17, the pairs of keyholes are spaced closer and farther away from the central axis to permit adjustment of the size of the tubular back brace 90. Thus, the back panel 92 is very much the same as the back panel 14, except for the character of the left and right tongues.

Figure 19:
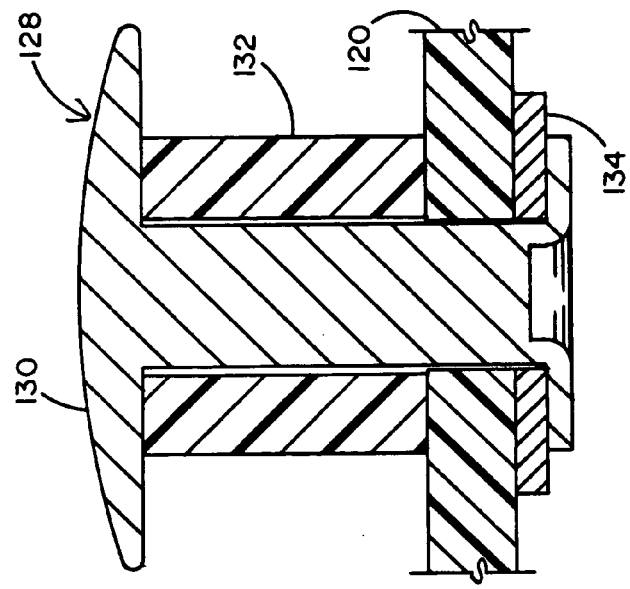
FIG. 19 is a perspective view of post 128 extending through body layer 120.
Figure 16:
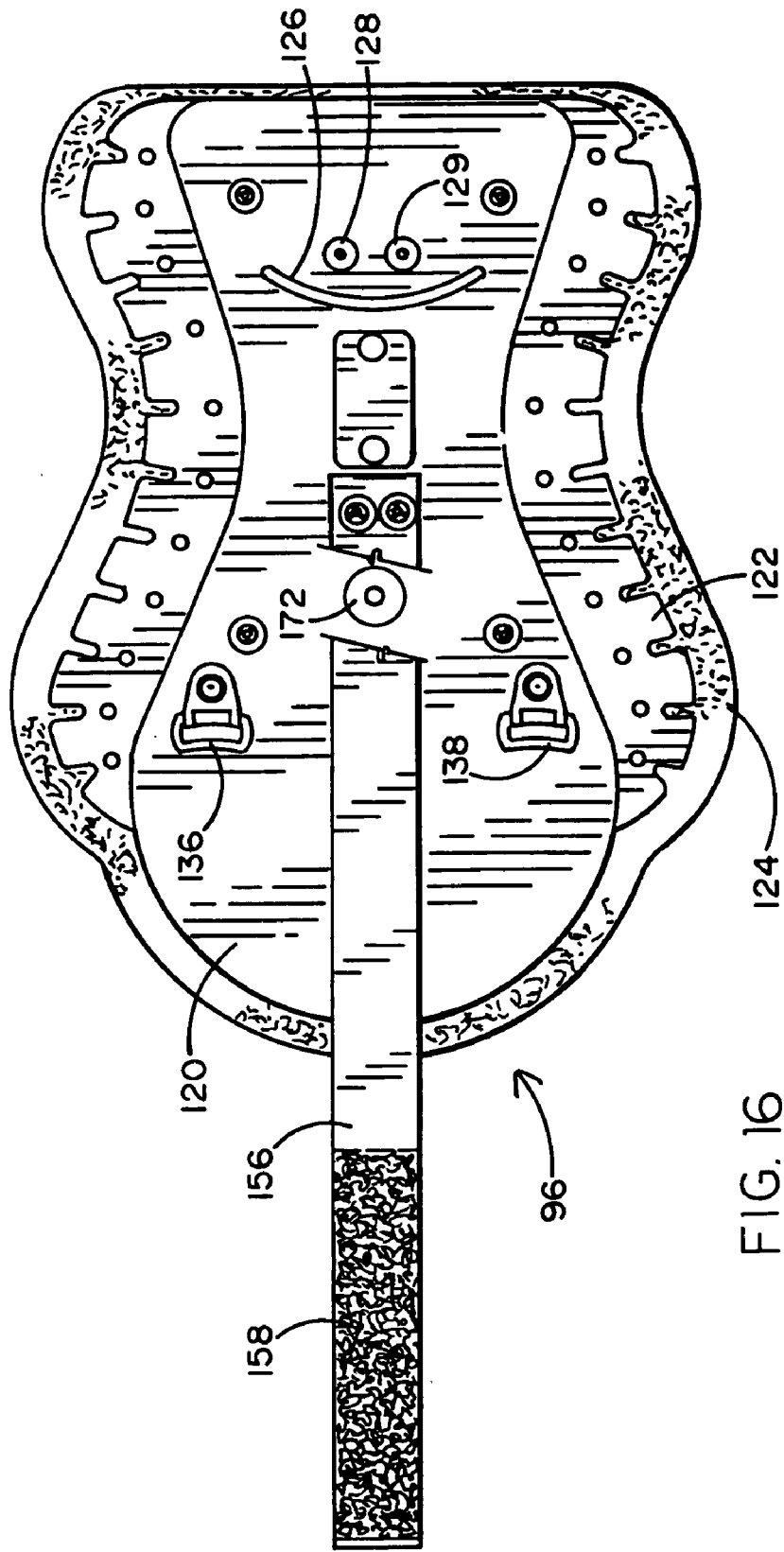
FIG. 16 is a plan view of the corresponding left side panel.

The left panel 96, shown in FIG. 16, is much like the left panel 16 shown in FIG. 1. The left panel 96 has a left body layer 120, which carries thereon a left pressure-spreading layer 122. A foam cushion layer 124 lies under the pressure-spreading layer and against the patient. The pressure-spreading layer has notches therein to regulate the firmness of the bending characteristics of the edges to provide greater comfort at the transition between the body layer 120 and the uncovered portion of the patient's torso. The significant difference between the left panel 96 and its corresponding left panel 16 in FIG. 1 is the adjustable attachment and securement with respect to the back panel. A slot 126 is provided which is slightly larger than the width of the tongue 108. The tongue 108 enters the slot, as seen in FIG. 14. Posts 128 and 129 are mounted behind the slot 126. The post 128 is shown in enlarged detail in FIG. 19, and the other posts are the same. As seen in FIG. 19, the central part of post 128 is a rivet having a head 130, which is sized to fit through the larger portion of the keyhole slot. Under the head, cylindrical tubular spacer 132 holds the head above the left body layer 120 a distance slightly greater than the thickness of the tongue 108. The spacer is smaller than the small portion of the keyhole opening in order to permit the shank of the post and the spacer 132 to slide into the smaller portion of the keyhole. In this position, the head 130 engages over that portion of the tongue 108 to hold it in place.

The post 128 extends through the left body layer 120 and through washer 134 and is riveted over the washer to securely the post in place. Since there are two such posts engaging in two corresponding keyhole slots, rotation of the overlapping panels with respect to each other is prevented. This is further prevented by the engagement of tongue 108 into slot 126 where it just barely fits in the width-wise direction, to constrain the left side panel and the back panel with respect to each other, both in the around-the-body direction where back brace compression can be achieved and in motion of the left side panel and back panel with respect to each other.

Attached to the left body layer 120, as far apart as practical in the up-and-down direction are top and bottom attachment clips 136 and 138. They are used in connection with retaining bands on the right panel during tightening and retaining the back brace in back bracing position.

Figure 15:
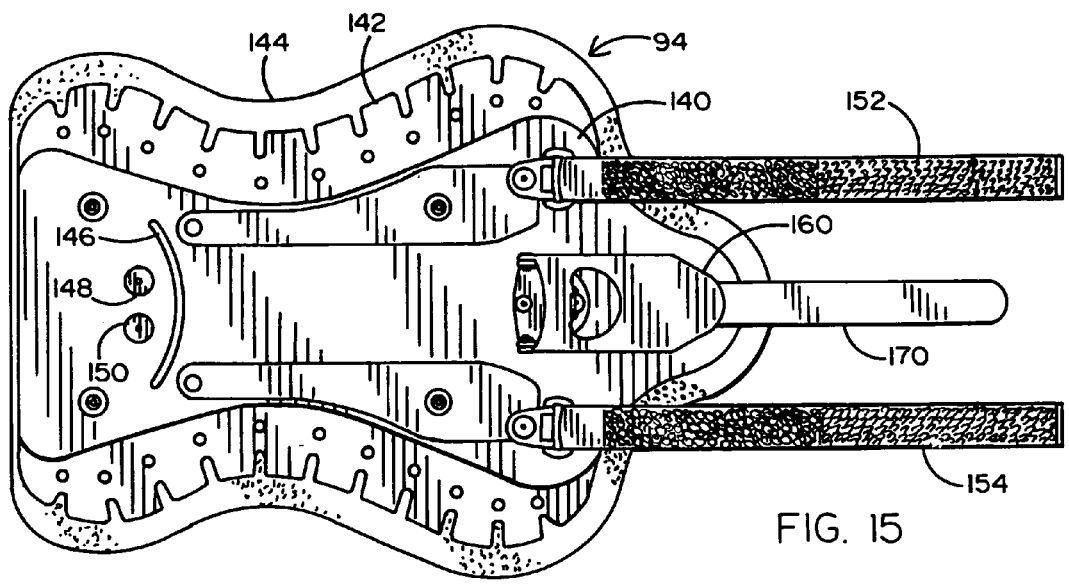
FIG. 15 is a plan view of the right side panel of the back brace of FIG. 14.

In general terms, the right panel 94, seen in FIG. 15, is similar to the left panel 96 and to the right panel 12. It has a principal layer 140 of the same characteristics as the layer 120. It carries a pressure-spreading layer 142 and a foam cushion layer 144. Furthermore, it has a slot 146 to receive the right tongue 110. The tongues 108 and 110 are of uniform width so that, over their entire length, they are closely engaged by the slot. The slot is sufficiently wide to permit adjustment, but suitably restrains width-wise motion of the tongue with respect to the side panels.

Two posts 148 and 150 are positioned adjacent the slot 146 to be engaged by one of the pairs of keyhole slots in the right tongue 110. This engagement is not seen in FIG. 14, but it is the same as the engagement shown therein. The tongue goes into the slot, and the posts engage in one of the pairs of keyhole openings. The circumferential size of the back brace 90 is adjusted by selecting the correct pair of keyhole openings to be engaged by the posts for a patient of particular size. Preferably, the left and right tongues 108 and 110 of the back panel should be engaged the same amount in the slots in the left and right side panels. Proper engagement permits the left and right side panels to overlap in the front when the back brace is tightened on the patient.

Upper and lower retaining bands 152 and 154, see FIG. 15, are secured to the principal layer 140 of the right side panel. They are spaced to engage through the upper and lower attachment clips 136 and 138 on the left panel 96, as seen in FIG. 14. The retaining bands have hook-and-loop fasteners so that, when they are engaged through the attachment clips and folded over, each can be attached to itself. In addition, tightening band 156 is secured to the left panel 96, as seen in FIG. 16. The tightening band also has hook-and-loop fastener structure 158 thereon so that it can be engaged around the bar of tightening lever 160 for successive tightening steps, as previously described with respect to the back brace 10. When the tightening band 156 is engaged around the crossbar the same as crossbar 86 and the tightening band is secured back upon itself, raising the lever pulls on the tightening band with mechanical advantage and pulls the left and right side panels together in overlapping relationship, as seen in FIG. 14. After the lever is pulled back to the position in FIG. 10, the upper and lower retaining bands 152 and 154 are tightened to hold the left and right side panels in place. The relative tightening of the retaining bands is dependent on the development of the patient. The tightening lever is again moved to the left, the tightening band 156 is retightened, and the lever 164 is pulled back. This is repeated until the desired tightness and configuration for development is achieved.

Since the left and right panels overlap in the front and are secured by spaced upper and lower retaining bands, and since both of the side panels are securely and non-rotatably attached to the back panel, a completely surrounding tubular back brace is created. Adjustability is available during the original fitting and can be employed if there is a substantial change in the configuration or development of the patient. However, once adjusted by the orthopedist, the back brace 90 usually retains its adjustment for a particular patient and, thus, acts like a one-piece, tubular back brace.

A donning strap 170 is attached to the layer 140 under the lever 160. The donning strap 170 has hook-and-loop fastener material thereunder. The left side panel 96 has fastener dot 172 thereon. This is of the opposite character of the hook-and-loop material of donning strap 170. In FIG. 16, the tightening band is broken away at the fastener dot 172 to provide its visibility. In actuality, the tightening band extends over the fastener dot which could not be directly seen. The purpose of the donning strap 170 and fastener dot 172 is to help the patient to put on his back brace. He wraps the back brace around his torso and, before any of the other closure fastenings are made, he applies the strap 170 to the fastener dot 172. This is sufficient to hold the back brace in place while he works on the closure system, including placing the upper and lower retaining bands through their attachment clips and engaging the strap 156 around the crossbar 86 of the tightening lever. Once those steps are completed, the donning strap has no further use. Indeed, it is hidden beneath the tightening band 156.

Figure 18:
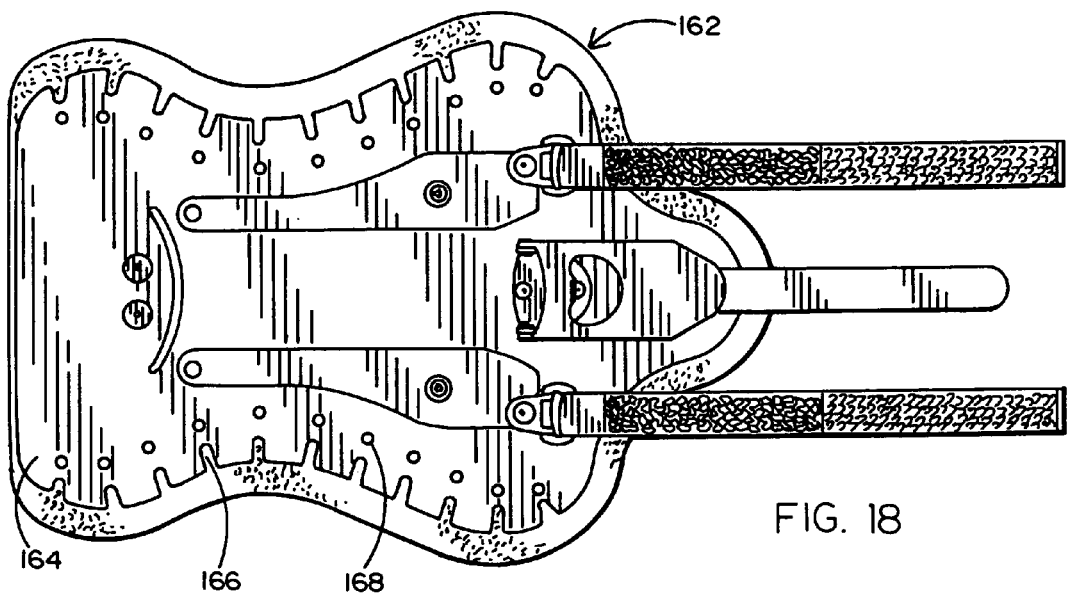
FIG. 18 is a plan view of another preferred embodiment of the left side panel, the right side panel being of corresponding configuration, comparable to FIG. 16.

The left and right side panels 96 and 94 both have the principal panel and the pressure-spreading layer. The pressure-spreading layer is positioned outside the foam cushioning layer. Each is of synthetic polymer composition material. If economy is important, a portion of the advantage of the notched edge of the pressure-spreading layer can be accomplished by choosing a lighter or more flexible polymer sheet layer for the principal layer and notching the edge thereof to achieve some of the benefits of reducing the sharpness of the edges. FIG. 18 shows a right side panel 162 which is of substantially the same configuration as the right side panel 94. The right side panel 162 has a principal panel layer 164 made of sheet synthetic polymer composition material of such thickness as to give significant strength and yet be sufficiently flexible to wrap around the torso of the patient, as described above. It carries the same retaining bands and tightening lever as the right side panel 94 shown in FIG. 15. The difference is that the function of the layers 140 and 142 in the side panel 94 are combined in the side panel 164. The side panel 164 has edge notches 166 to soften the edge and permit some outward bending of the sections between the notches. In addition, the edge can be made even softer in selected locations by cutting the notches down to the holes 168. One hole lies below each one of the notches. The holes make it easy achieve symmetry of the edge flexibility. The holes also make it easy to make the modifications while the back brace is on the patient. The holes aid in resisting tearing of the panel material, which might happen if cutting below the notches is not limited by the presence of the holes.

This invention has been described in its presently preferred embodiments, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A back brace comprising a back piece that extends across a midline of a wearer, a left panel and a right panel coupled to the back piece for extending across the lateral sides of a wearer a left pressure-spreading layer under a left panel and a right pressure-spreading layer under the right panel, said left and right pressure-spreading layers having edges extending above the left and right panels, said left and right pressure-spreading layers being more flexible than said left and right panels and said pressure-spreading layers having notches extending inwards from the edges thereof, and the back piece and left and right panels sized and dimensioned to fit about a waist of a wearer.

2. The back brace of claim 1 wherein the left and right panels overlap with and are firmly coupled to the back piece.

3. The back brace of claim 2 wherein the left and right panels are coupled to the back piece in a non-hinging manner.

4. The back brace of claim 2 wherein the left and right panels are coupled to the back piece in a non-pivoting manner.

5. The back brace of claim 2 wherein the left and right panels are coupled to the back piece in a non-permanent manner.

6. The back brace of claim 2 wherein the left and right panels are coupled to the back piece in a permanent manner.

7. The back brace of claim 1 further comprising at least one adjustment hole aligned with each of the plurality of notches.

8. The back brace of claim 1 further comprising at least two holes aligned with at least one of the plurality of notches.

9. The back brace of claim 1 wherein the inwardly extending notches provide a corresponding plurality of edge tabs, and at least one of the edge tabs has a substantially uniform thickness along its length.

10. The back brace of claim 1 wherein the back piece further comprises a sacral window with an adjacent malleable frame.

11. The back brace of claim 10 wherein the frame comprises a metal.

12. The back brace of claim 10 wherein the window is sized and dimensioned such that a fitter can observe and adjust a fit of the brace against a back side of a wearer, above the wearer's sacrum.

13. The back brace of claim 2 wherein at least one of the back piece and left and right panels and includes the pressure spreading layer disposed between the panel and a cushion.

14. The back brace of claim 2 wherein the left and right panels are incrementally adjustable relative to each other using an adjustment structure associated with individual increments, and comprising visual indicators indicating a waist size associated with each of the increments.

15. The back brace of claim 14 wherein each increment has at least two adjustment structures associated with it, the structures being adapted to inhibit rotation of the two left and right panels relative to each other.

* * * * *